US005654150A

United States Patent [19]

King et al.

[11] Patent Number: 5,654,150

[45] Date of Patent: Aug. 5, 1997

[54] METHOD OF EXPRESSION CLONING

[75] Inventors: Randall W. King, Brookline; Kevin D. Lustig, Cambridge; P. Todd Stukenberg, Jamaica Plain; Marc W. Kirschner, Newton, all of Mass.

[73] Assignees: President and Fellows of Harvard College; Harvard University, Office of Technology and Trademark Licensing, both of Cambridge, Mass.

[21] Appl. No.: 475,219

[22] Filed: Jun. 7, 1995

[51] Int. Cl.$^6$ .............................. C12Q 1/68; C12P 21/06
[52] U.S. Cl. .............................. 435/6; 435/68.1; 935/19; 935/81
[58] Field of Search .......................... 435/320.1, 68.1, 435/6, 69.1

[56] References Cited

U.S. PATENT DOCUMENTS 4,675,285   6/1987   Clark et al. .......................... 435/6

OTHER PUBLICATIONS

Munroe et al. (1995) Proc. Natl. Acad. Sci. USA 92:2209–13.
Ward et al. (1995) J. Virol Methods 53:263–72.
Gehlert et al. (1996) Mol. Pharmacol. 49:224–8.
Boll et al. (1996) Proc. Natl. Acad. Sci. USA 93:284–9.
Bertran et al. (1992) Proc. Natl. Acad. Sci. USA 89:5601–5.
Brudnak et al., 66 Bio Techniques 14, No. 1 (1003).
Kieffer, Gene (1991) 109: 115–119.
Sager et al., The FASEB Journal (1993) 7: 964–970.
Kluxen et al., Analytical Biochemistry (1993) 208: 352–356.
Dalboge et al., Mol Gen Genet (1994) 243: 253–260.
Brakenhoff et al., Analytical Biochemistry (1994) 218: 460–463.
Ross et al., J. Biol. Chem. (1991) 266: 20283–20289.
Sasaki et al., Nucleic Acids Research (1994) 22: 987–992.
Rayner et al., Molecular and Cellular Biology (1994) 14:880–887.
Miki et al., Proc. Natl. Acad. Sci. (1991) 88: 5167–5171.
Beckmann et al., The EMBO Journal (1994) 13:3757–3762.
Alderson et al., J. Immunol. (1994) 24:2219–2227.
Seed et al., Proc. Natl. Acad. Sci. (1987) 84: 3365–3369.
Mougneau et al., Science (1995) 268: 563–566.
Spengler et al., Nature (1993) 365: 170–175.
Brunden et al., J. Theor. Biol. (1990) 144: 145–154.
Promega Technical Bulletin, (1992) (1993), 26, 1–18.

Primary Examiner—Stepanie W. Zitomer
Assistant Examiner—Amy Atzel
Attorney, Agent, or Firm—Hale and Dorr LLP

[57] ABSTRACT

The present invention provides improvements in the expression cloning method for isolating novel cDNA clones. In particular, in the expression cloning method comprising the steps of preparing a cDNA library from a cell that expresses a desired protein; inserting the cDNA library into an expression vector; inserting the cDNA library into bacterial cells and culturing the bacterial cells to produce individual bacterial colonies; collecting pools of a predetermined number of individual bacterial colonies; isolating the cDNAs contained in the pools; expressing proteins encoded by the cDNAs; and detecting the desired protein, positive clones may be efficiently and cost-effectively obtained by collecting pools of about 100 individual bacterial colonies and expressing proteins encoded by the cDNAs in the pools in vitro.

15 Claims, No Drawings

METHOD OF EXPRESSION CLONING

FUNDING

This invention was funded by the National Institutes of Health. The Government has certain rights in the invention.

FIELD OF THE INVENTION

The present invention relates to improvements in the expression cloning method of identifying and isolating full-length nucleic acids encoding complete proteins.

BACKGROUND OF THE INVENTION

During the 1970's and 1980's a number of techniques became available for identifying and isolating nucleic acids that encode proteins. Such techniques, or cloning methods, traditionally involved lengthy multistep processes which were based on knowledge of protein structure, availability of an antibody specific to the protein, or on ability to isolate an mRNA species corresponding to the protein. The traditional cloning methods were labor-intensive and were highly dependent on the abundance of the protein or nucleic acid within the cell.

U.S. Pat. No. 4,675,285 discloses a cloning method which is based solely on the ability to detect expression of a protein in an assay. In this method, a cDNA library is prepared from a cell that expresses the desired protein. The cDNA library is then inserted into an isolation (or transient) expression vector plasmid which is capable of directing DNA replication in bacterial cells in addition to being capable of directing both DNA replication and protein expression in mammalian cells. The isolation expression vector plasmid containing the cDNA library is transformed into bacteria, and individual colonies of bacteria containing the plasmids are obtained by diluting the bacterial culture and spreading the dilutions onto a solid surface of nutrient agar contained within a Petri dish or plate. By virtue of the dilutions, single bacteria can adhere to the agar surface and can be grown to yield discreet and easily identified colonies. Each bacterial colony contains a single isolation expression vector/cDNA plasmid. In the method of U.S. Pat. No. 4,675,285, this step yields about 2000 bacterial colonies per plate.

In the method of U.S. Pat. No. 4,675,285, the bacterial colonies are then lifted onto nitrocellalose master filters and replica plated. A predetermined number of bacterial colonies on each replica filter is combined to form a heterogeneous pool of colonies, and the plasmid DNA is isolated from each pool. The plasmid DNA is then transfected or microinjected into a mammalian host cell and the proteins encoded by the cDNAs are expressed. Expression of a particular desired protein is detected using a detection system or assay. However, for the assay to be sensitive and specific, the cell type used to express the desired protein must itself be devoid of the activity of interest, which severely limits the range of assays that can be used to detect the desired protein.

In the method of U.S. Pat. No. 4,675,285, the number of bacterial colonies per heterogeneous pool is determined on the basis of the yield of protein from the mammalian host cell and by the sensitivity of the detection system or assay used to detect the expressed product. A tenfold reduction factor is applied to compensate for variability in the size of the individual bacterial colonies within the heterogeneous pools and for day-to-day variability in growth of the mammalian host cells. Using this method for predetermining pool sizes, U.S. Pat. No. 4,675,285 discloses detection of single colonies containing cDNAs encoding several desired proteins, within pools of 500–1000 heterogeneous colonies. U.S. Pat. No. 4,675,285 discloses that isolation of the plasmid DNA from each individual bacterial colony is generally impractical, since large numbers of cDNA clones generally must be assayed in order to isolate a particular cDNA, especially if the cDNA corresponds to a rare mRNA.

Many known expression cloning methods, including that of U.S. Pat. No. 4,675,285, are dependent on transient gene expression in a mammalian host cell. Cells which support transient gene expression allow extrachromosomal replication of the isolation expression vector/cDNA plasmid, resulting in high copy numbers of the plasmid and correspondingly high levels of protein expressed from the cell. Most commonly the African green monkey kidney COS cell line is used for this purpose. As set forth in U.S. Pat. No. 4,675,285, COS cells exhibit variability in their day-to-day behavior which can affect protein expression levels and thus the outcome of the expression cloning experiments. In addition, transient gene expression in cells requires use of large mounts of highly purified cDNA to transfect the cells, making the technique laborious and expensive. Furthermore, the technique is time-consuming, since the cells require several days of growth to express detectable levels of protein. Successful expression of a particular gene in COS cells is not guaranteed, especially if expression of the gene is subject to strict regulatory controls derived from the cell in which it naturally occurs, or if the gene is not derived from a mammal. Many transfectable eukaryotic cells do not support transient gene expression, and thus use of transient gene expression limits the number of genes which may be identified by the expression cloning approach.

In vitro expression systems contain little or no endogenous mRNA, allowing specific labeling of the proteins encoded by cDNAs added to the systems. Such systems also lack many of the biological activities that can be present in cells, allowing a broad range of assays to be employed to detect expressed proteins. Although use of in vitro expression of the isolation expression vector/cDNA is suggested in U.S. Pat. No. 4,675,285, this technique has not been generally adopted by those of skill in molecular biology for expression cloning. A principal reason for this is that the number of heterogeneous cDNAs in the large pools of U.S. Pat. No. 4,675,285 would not yield discreet and easily detectable expressed proteins in an in vitro translation system.

SUMMARY OF THE INVENTION

The present inventors have for the first time recognized that many of the disadvantages of expression cloning using transient gene expression in cells can be overcome by subdividing the cDNA library into much smaller pools than has been previously taught and by using in vitro systems to express the small pools of cDNAs. The present invention therefore provides a more efficient, versatile, and cost-effective expression cloning method than has been previously possible.

In one embodiment, the invention provides: in the method of identifying a cDNA encoding a desired protein, which method comprises the steps of preparing a cDNA library from a cell that expresses the desired protein; inserting said cDNA library into an expression vector; inserting said cDNA library into bacterial cells and culturing said bacterial cells to produce individual bacterial colonies; collecting pools of a predetermined number of individual bacterial colonies; isolating the cDNAs contained in the pools; expressing proteins encoded by the cDNAs; and detecting the desired protein, the improvement comprising:

a) collecting pools of about 100 individual bacterial colonies; and b) expressing proteins encoded by the cDNAs in the pools in vitro.

DESCRIPTION OF THE PREFERRED EMBODIMENTS

In accordance with the present invention, any method may be used to prepare a cDNA library from a cell that expresses the desired protein. Preferably, the cDNA library is prepared by extracting the mRNA from a culture of cells that express the desired protein, using known methods, for example, isolation of polyadenylated (poly $A^+$) RNA. Kits for isolating poly $A^+$ RNA are commercially available, for example, the PolyATract™ is available from Promega Corporation (cat. #Z5420). The mRNA thus extracted may be enriched for mRNAs corresponding to the desired protein, for example, by size fractionation on electrophoretic gels, by isolation of membrane bound mRNAs if such mRNAs encode the desired protein, by hybrid selection procedures, and the like. The cDNAs corresponding to the mRNAs are prepared using a reverse transcriptase for first strand synthesis and a DNA polymerase for second strand synthesis. Methods for using reverse transcriptase and DNA polymerase to make cDNA are well known in the art. Kits for performing these techniques are commercially available, for example, the Superscript II™ kit (Gibco-BRL, Gaithersburg, Md., U.S.A., cat. #18248-013), the Great Lengths cDNA Synthesis Kit™ (Clontech, Palo Alto, Calif., U.S.A., cat. #K-1048-1), the cDNA Synthesis Kit (Stratagene, La Jolla, Calif., U.S.A., cat. #200401), and the like. The cDNAs may then be ligated to linker DNA sequences containing suitable restriction enzyme recognition sites. Such linker DNAs are commercially available, for example, from Promega Corporation, Madison, Wis., U.S.A. and from New England Biolabs, Beverly, Mass., U.S.A., and the particular linker used may be selected to conform to the protocol being used. The cDNAs may be subjected to restriction enzyme digestion, size fractionation, or any other suitable method, to enrich for full-length cDNAs within the library. Alternatively, a commercially available cDNA library such as the Human Brain Library (Clontech, Palo Alto, Calif., U.S.A., cat. #HL3002S), the Human Liver Library (Clontech, Palo Alto, Calif., U.S.A., cat. #HL3006S), and the like may be used in the method of the invention.

In the next step of the method of the invention, the cDNA library is inserted into an expression vector which contains sequences that direct DNA replication in a prokaryotic cell and which also contains sequences that direct DNA transcription and mRNA translation in an in vitro system. This insertion step may optionally be performed in such a way that the cDNAs are inserted into the expression vector in a preferred direction. Any expression vector capable of directing DNA replication in a prokaryotic cell and of directing DNA transcription, and mRNA translation in an in vitro system may be used in practicing the method of the invention. Many such vectors are commercially available, for example, the pSP64 vector (Promega Corporation, Madison, Wis., U.S.A., cat. #P1091); the pGEMEX-1 vector (Promega Corporation, Madison, Wis., U.S.A., cat. #P2211), the pGEMEX-2 vector (Promega Corporation, Madison, Wis., U.S.A., cat. #P2551), and the like. Construction of expression vectors is within the level of ordinary skill in molecular biology, as indicated in U.S. Pat. No. 4,675,285, as is construction of expression vectors containing DNA sequences which direct transcription and translation in in vitro systems.

In the next step of the method, the expression vector containing the cDNA library is then inserted into bacterial cells, using known methods such as transformation, described in Sambrook, J. et at., *Molecular Cloning: a Laboratory Manual*, 2nd Ed., Cold Spring Harbor Press (Cold Spring Harbor, N.Y., 1989). Any bacterial cell may be used for this step of the invention, so long as the cell is capable of taking up DNA. Preferably, *Escherichia coli* is used to perform this step, and when transformation is used, the *E. coli* cells are preferably treated in such a way that they are competent for transformation. Competent *E. coli* cells are commercially available, for example, ElectroMAX™ DH10B cells are available from Gibco-BRL, Gaithersburg, Md., U.S.A. After the expression vector containing the cDNA library is inserted into the bacterial cells, the cells are cultured to produce individual colonies. Methods and reagents for culturing bacterial cells to select for transformants and to produce individual bacterial colonies are well known in the art. Preferably, the cultured cells are diluted using a diluent medium and samples of the dilutions are plated onto a solid surface of nutrient agar to obtain about 300 individual colonies per 85 $cm^2$ culture plate.

In the next step of the method, pools of about 100 individual bacterial colonies are collected. Preferably, the pools are collected in accordance with the invention by transferring a small sample of a single bacterial colony into each well of a microtiter plate. The bacterial samples are incubated in a nutrient medium at a temperature and for a time suitable to amplify the number of bacterial cells and correspondingly, the number of cDNA-containing plasmids within the bacterial cells. After amplification, samples of bacteria from each well of a microtiter plate are collected and combined to form a pool.

Plasmids containing the cDNAs contained in the pools are then isolated using known methods such as the miniprep method described in Sambrook, et at. supra. Kits for performing plasmid minipreps are commercially available, for example, from Promega Corporation, Madison, Wis., U.S.A. (the Wizard Miniprep System, catalog #A7100).

The proteins encoded by the cDNA pools are then expressed in vitro using known methods. Kits for performing coupled transcription and translation are commercially available, for example, from Promega Corporation, Madison, Wis., U.S.A. (the TnT™ Coupled Reticulocyte Systems, catalog numbers L4600, L4610, L4950, L5010, K5020). Other in vitro translation systems may also be used, for example, systems which employ wheat germ extracts, and the like. The in vitro translation products may be labeled with radioactive amino acids such as $^{35}$S-methionine to facilitate high-sensitivity detection. Alternatively, the in vitro translation products may be labeled with chemically modified amino acids such as biotinylated lysine to facilitate both detection and purification of the expressed protein using a solid substrate such as streptavidin-coated beads. Kits for such chemical modification are commercially available, for example, the Transcend™ system from Promega Corporation, Madison, Wis., U.S.A.. The in vitro translation products may optionally be modified using purified modifying enzymes such as kinases, using chemical modifying reagents, or using crude cellular lysates.

The desired protein is then detected in an assay. Any suitable assay may be used in accordance with the present invention, so long as the assay is capable of detecting some characteristic of the expressed protein. Such assays may be based on the binding characteristics of the desired protein.

For example, pools expressed in vitro may be separated by sodium dodecyl sulfate-polyacrylamide gel electrophoresis (SDS-PAGE), transferred to filters, and probed with an antibody which is known to bind to the desired protein or to proteins having homology to the desired protein, using the western blotting procedure. Alternatively, pools may be expressed in vitro in the presence of a radioactive label such as $^{35}$S-methionine, immunoprecipitated, and the immunoprecipitates analyzed by SDS-PAGE and autoradiography. A co-immunoprecipitation assay may be used which employs an antigenie protein that binds to known proteins having similar activity to that of the protein of interest. In the co-immunoprecipitation assay, a crude lysate containing the antigenie protein is mixed with labeled in vitro translated proteins encoded by the pool. The complex is then immunoprecipitated with a suitable antibody, washed, eluted, and analyzed by SDS-PAGE and autoradiography.

Assays which detect interactions between the desired protein and a known protein may also be used to detect a desired protein in accordance with the present invention. The known protein may be purified and immobilized on a solid substrate such as a resin. Radioactively labeled in vitro translated proteins derived from the pools are added to the immobilized protein, and the complex is washed, eluted, and analyzed by SDS-PAGE and autoradiography.

If the desired protein is a nucleic-acid binding protein such as a transcription factor or an origin recognition component, the specific DNA or RNA recognition sequence may be immobilized on a solid substrate. Radioactively labeled in vitro translated proteins derived from the pools may be added to the immobilized nucleic acid and binding is analyzed by SDS-PAGE and autoradiography.

Genes encoding cytoskeletal proteins may be detected in accordance with the present invention by incubating radioactively or fluorescently labeled in vitro translated proteins derived from the pools with polymerized microtubules or actin filaments Novel cytoskeletal proteins that interact remain associated with the microtubules or filaments after centrifugation or electrophoresis.

Assays based on enzymatic or biological activity may also be used to detect the desired protein in accordance with the invention. For example, pools of in vitro translated proteins could be tested for their ability to serve as growth or differentiation factors by incubating each pool with tissue culture cells known to grow or differentiate in response to specific stimuli.

The pools of the invention may also be tested for the presence of an enzymatic activity, using an assay for the particular enzymatic activity. In this way, novel enzymes, including novel subunits of multisubunit enzymes, may be identified. Pools of in vitro translated proteins may be tested in accordance with the invention for their ability to complement known multiple component protein complexes. Such a multiple component protein complex, for example, a cyclin degradation system, may be biochemically fractionated and a particular component of the complex removed. The pool of translated proteins may be added to the remaining fractions of the complex and assayed for ability to restore the biological activity of the complex. In another embodiment, pools of in vitro translated proteins may be tested for their ability to function as microtubule or actin-based motors, for example, by labeling pool proteins with biotinylated lysine, binding the proteins to streptavidin immobilized on beads, and assaying the ability of the beads to move along microtubules or actin filaments in vitro.

Alternatively, labeled pools of in vitro translated proteins may be incubated with crude lysates of the cells from which the cDNA library was isolated. The occurrence of a specific posttranslational modifications such as phosphorylation, proteolytic cleavage, glycosylation, and the like, may be analyzed. In this manner, intracellular signals which mediate specific events such as transport into different cellular compartments or progression to a particular developmental stage may be identified. For example, Examples 1 through 5 below set forth isolation of novel and known proteins which are modified through phosphorylation by mitotic kinases.

The method of the invention also allows convenient identification both of novel proteins and of novel isoforms of known proteins. Identification of such isoforms may facilitate resolution of the etiology of genetic diseases.

Novel types of enzymes may be developed using the method of the invention. For example, a DNA encoding a known enzyme with a given substrate specificity may be mutated using known methods of mutagenesis, and the mutants thus obtained may be cloned as set forth above and tested for activity against previously suboptimal substrates. Multiple rounds of this process might allow one to evolve a novel enzymatic activity, for example, by converting a ribonuclease into a deoxyribonuclease. A variation of this approach may be used to determine the causes of drug or antibiotic resistance. A DNA encoding the target enzyme may be mutated and cloned as above, and the in vitro-translated pools of protein may be assayed in the presence of the drug or antibiotic. Pools containing resistant enzymes may be subdivided to obtain single clones, the DNA isolated, sequenced, and compared to the unmutated DNA to determine the cause of resistance. Novel drugs and antibiotics may also be tested against panels of resistant enzymes thus identified.

The method of the invention may also be used to design inhibitors of enzymes involved in disease states such as viral proteases. A DNA encoding a proteinaceous substrate of the target enzyme could be mutagenized and then screened to identify mutants capable of inhibiting the target enzyme's activity in the presence of wild-type substrate. Alternatively a DNA encoding a random protein sequence could be mutagenized to identify an inhibitor. Multiple rounds of mutagenesis could be applied to optimize the inhibitor's activity.

The following examples illustrate the preferred modes of making and practicing the present invention, but are not meant to limit the scope of the invention since alternative methods may be used to obtain similar results.

EXAMPLE 1 cDNA LIBRARY CONSTRUCTION

Hyperdorsalized lithium chloride-treated *Xenopus laevis* embryos (Kao, K. et al., *Meth. Cell Biol.* (1991) 36, 271–284) were prepared and frozen at −80° C. Total RNA was isolated from frozen tissue using RNAzol B (Tel-Test, Friendswood, Tex., U.S.A., cat. #CS-1 05). Poly(A)$^+$RNA was selected twice using the PolyATract kit (Promega Corporation, Madison, Wis., U.S.A., Cat. Z5420). A directional cDNA library was constructed following the instructions for the SuperScript Plasmid System (Gibco-BRL, Gaithersburg, Md., U.S.A., Cat. #18248-013). An oligo(dT) primer-adapter containing an XbaI site (Promega Corporation, Madison, Wis., U.S.A., Cat. #C1011) was used to prime first strand synthesis. Nick translational replacement of the mRNA was then used to synthesize the second strand cDNA. After ligation to EcoRI adapters, the cDNA was digested with XbaI and size-fractionated on a Sephacryl S-500 HR column (Gibco-BRL, Gaithersburg, Md., U.S.A., Cat. #18092-015) to remove residual EcoRI adapters and cDNA smaller than 0.5 kb. The size-selected cDNA was cloned directionally into the EcoRI and XbaI sites of the eukaryotic expression plasmid pCS2+(Rupp, R. A. W., et al., *Genes Dev.* (1994) 8, 1311–1323), a vector that allows direct in vitro translation of cloned cDNAs, and ligation products were introduced into ElectroMAX DH10B *E. Coli* cells (Gibco-BRL, Gaithersburg, Md., U.S.A., Cat. #18290-015) by electropotation. The transformed bacteria were incubated at 37° C. for one hour prior to storage at –80° C.

The expression library consisted of approximately 1.7× $10^6$ independent transformants and had a titer of approximately 600 bacteria per microliter. To determine the range of cDNA insert sizes, plasmids from 100 individual bacterial colonies were prepared separately, digested with EcoRI and XbaI, and then resolved on a 1% agarose gel. The cDNA insert size ranged from 0.6 kb to 4 kb and the average size was 1.3 kb.

EXAMPLE 2

CONSTRUCTION OF cDNA POOLS

To prepare pools of library DNA for expression in vitro, aliquots of frozen transformed cells were thawed and diluted in 2X YT medium (Sambrook, J. et al., supra.) Approximately 300 bacterial transformants were plated onto an 85 $cm^2$ LB-agar plate (Sambrook, J. et al., supra) supplemented with 100 µg/ml carbenecillin. After an overnight incubation at 37° C., a toothpick was used to transfer a small sample of each colony into a single well of a 96-well plate; each well of the 96-well plate contained 200 µl of LB supplemented with 100 µg/ml carbenicillin. The plate (containing 96 independent transformants) was wrapped in parafilm to prevent medium evaporation and incubated overnight at 37° C. To construct pools of 96 plasmids, a multipipettor was then used to sample approximately 100 µl from each well of a single plate. One-hundred µl of LB containing 40% glycerol was added to the remaining 100 µl in each well and the 96-well plates were stored at –80° C. Plasmid DNA representing the 96 independent transformants pooled from each plate was purified using the Wizard miniprep system (Promega Corporation, Madison, Wis., U.S.A., Cat. #A7100).

EXAMPLE 3

EXPRESSION OF PROTEINS in Vitro

Library pools of cDNAs (1 µg each) were translated in vitro in a 10 µl reaction volume employing the SP6-TNT coupled transcription/translation system (Promega Corporation, Madison, Wis., U.S.A., Cat. #L4600 ) according to the manufacturers protocol, using [$^{35}$S]-methionine to label the translated proteins. One µl of each 10 µl translation reaction was added to 25 µl of 2×SDS sample buffer (16% glycerol (Fisher Scientific, Pittsburg, Pa., U.S.A.), 1.7% sodium dodecyl sulfate (Sigma St. Louis, Mo., U.S.A.), 83 mM dithiothreitol, 0.03% bromphenol blue (Sigma St. Louis, Mo., U.S.A.)), boiled for 5–10 minutes, and analyzed by 12% SDS-polyacrylamide gel electrophoresis. A typical translation reaction of a single pool yields 10–35 distinct radioactively-labeled bands on an autoradiogram of a 12% polyacrylamide gel.

EXAMPLE 4

IDENTIFICATION OF MPM-2-PHOSPHORYLATED PROTEINS

Changes in cellular morphology which occur during mitosis are believed to be orchestrated by a series of protein kinases known as the mitotic kinases which specifically phosphorylate substrate proteins. The monoclonal antibody MPM-2 (Davis, F. M., et at., (1983) *Proc. Natl. Acad. Sci. U.S.A.* 80, 2926–2930) recognizes a phosphoepitope on approximately 100 proteins that become phosphorylated as cells enter mitosis. Immunofluorescent staining of cells with MPM-2 rises and falls during mitosis, and mitotic structures such as kinetochores, centrosomes, polar microtubules, and the central axis of chromosomes are recognized by MPM-2. The MPM-2 antibody was used to detect *Xenopus laevis* embryo proteins containing this phosphoepitope, and thus to identify possible mitotic kinase substrates.

Because the MPM-2 antibody is of the murine IgG$_1$ isotype, it has a low affinity for protein A, and it is necessary to use the following procedure to immobilize MPM-2 on proteinA agarose beads. A slurry containing 5 ml of Affigel protein A agarose (Biorad, Hercules, Calif., U.S.A., cat. #153-6153) was poured into a small column (1×10 cm) and the column packed at room temperature by gravity flowing buffer through the resin until the buffer begins to enter the gel. The column was equilibrated with 15 mls of MAPSII binding buffer (Biorad, Hercules, Calif., U.S.A., Cat. #153-6160). Two ml of MPM-2 ascites was clarified by centrifugation at 13,000 RPM for ten minutes in a Sorvall MC12V centrifuge. The supernatant containing the immunoglobulins was diluted in 4 ml of MAPSII binding buffer and was applied to the equilibrated column. The flow-through was collected and reapplied to the column to ensure maximum binding of the antibody to the beads. The beads were then washed in 50 ml of MAPSII binding buffer, followed by 75 ml of Tris-Buffered Saline (TBS: 20 mM Tris pH 7.6, 150 mM NaCl). The beads were resuspended in 5 ml of TBS, transferred to a 15 ml conical tube and stored at 4° C. until use. Prior to use, 15 µl aliquots of beads were washed in 500 µl of EB (80 mM Sodium Beta-glycerophosphate (Sigma, St. Louis, Mo., U.S.A.), 20 mM EGTA, 15 mM MgCl$_2$ (Sigma, St. Louis, Mo., U.S.A.)) and resuspended in 10 µl of EB.

A. MPM-2-Reactive Proteins in Translated cDNA Pools

Pools of Xenopus cDNAs produced as set forth in Examples 1 and 2 were translated as in Example 3 and incubated in a mitotic extract derived from Xenopus eggs, which contains mitotic kinases. For example, 4 µl of the in vitro-translated Xenopus proteins derived from each pool produced in Examples 1 and 2 were incubated for 20 minutes at 20° C. with 4 µl of a Xenopus egg interphase extract (Murray, A. W., *Mol. Cell Biol.* (1991) 36, 581–605) which had been driven into mitosis (Murray, supra) by the addition of Glutathione-S-transferase-Xenopus cyclin B fusion protein, in some cases in the presence of 1 µM okadaic acid (Calbiochem, San Diego, Calif., U.S.A.) and 0.2 mM EGTA (Sigma, St. Louis, Mo., U.S.A.).

Proteins containing the MPM-2 phosphoepitope were then immunoprecipitated using the MPM-2 antibody which had been immobilized on protein A-agarose beads as set forth above. The MPM-2 phosphoepitope-containing Xenopus proteins were added to 15 µl of immobilized MPM-2 antibody and incubated at 4° C. for 1–2 hours with rocking. Two hundred fifty µl of Wash C (1M NaCl, 1% NP40 (Sigma, St. Louis, Mo., U.S.A.) and 5 mM NaF in EB) was added, the mixture vortexed briefly, and then centrifuged at 13,000 RPM for 10 seconds in a Sorvall MC12V microcentrifuge. A 40 µl aliquot of the supernatant fraction was mixed with 10 µl of 5x sample buffer (Sambrook, J. et al., supra) and retained for analysis. The remaining supernatant was aspirated and the beads washed by adding 250 µl of Wash C, vortexing, centrifuging at 13,000 RPM for ten seconds, and aspirating the supernatant. The wash step was repeated four times using 500 µl of Wash C. Prior to electrophoretic analysis, the washed beads were boiled for 5–10 minutes in 25 µl of 2X Sample buffer.

Samples were analyzed by SDS-polyacrylamide gel electrophoresis using a 12% polyacrylamide Gels were then fixed in 40% methanol, 5% acetic acid for 20 minutes, and the gel was dried onto Whatman 3 MM paper and exposed on Kodak XAR X-ray film for three days with an intensifying screen at –80° C.

Under stringent washing conditions, most of the proteins remain in the immunoprecipitation supernatant. However, approximately one of every fifteen pools exhibited a band which strongly binds the MPM-2 beads. A similar pattern is observed when the known MPM-2 epitope-containing proteins cdc25 and wee1 were translated in vitro and analyzed in a similar manner.

B. Secondary Screen

A single pool was analyzed for MPM-2-reactive proteins which were present during mitosis but not present during interphase. MPM-2 immunoprecipitated proteins in a 4 µl aliquot of in vitro-translated proteins from Example 3 which had been incubated with 4 µl of an interphase Xenopus egg extract, were compared with an aliquot which had been incubated with a mitotic extract as set forth in Example 5A. The MPM-2 epitope containing proteins were analyzed on a 5–15% gradient polyacrylamide gel and autoradiographed as set forth above. Three proteins were detected in the mitotic extract sample which were not detected or detected at minimal levels in the interphase extract sample.

EXAMPLE 5

ISOLATION OF SINGLE CLONES

Once a positive pool was identified, it was necessary to subdivide the original pool of 96 clones in order to identify the single cDNA that conferred activity. This was accomplished by subdividing the original, frozen 96-well plate into a two-dimensional array. Such an array makes it possible to assay only 20 samples to determine which of the 96 wells contained the active cDNA. First, a replica of the original plate was created by using a multipipettor to transfer a small sample of frozen bacteria from each well into another 96-well plate. This replica plate, containing 200 µl of LB medium per well, was placed at 37° C. and incubated overnight to allow growth of the bacteria. Each 96-well plate consists of eight rows (1–8) and twelve columns (A–L). Fifty µl was removed from each of the wells in a single row and pooled together. This process was repeated for each row and for each column, generating a total of 20 samples (8 rows plus 12 columns). The 20 samples were grown for an additional two hours and plasmid DNA was then purified using the Wizard miniprep system (Promega Corporation, Madison, Wis., U.S.A., Cat. #A7100). Biological assays were carried out using these 20 pooled sets of cDNA clones. The single cDNA conferring activity is found in the single well that is common to both the active row and the active column. For example, if Row 1 and Column 1 are positive, then the active cDNA clone is found at the intersection point of Row 1 and Column 1. The final step of the procedure is to verify that the single well contains the active cDNA and that the activity is conferred by a single clone. This is accomplished by replating the bacteria from the active well and picking a single colony from the plate. This single colony is amplified and used to prepare plasmid DNA, which is then tested as follows.

Each of the single positive clones was confirmed to be phosphorylated in a mitosis-specific manner as follows. Each clone was in vitro-translated in a 10 µl reaction and divided into three aliquots. One aliquot was combined with 3 µl of a cycloheximide-presoaked activated Xenopus egg extract (an interphase extract); one aliquot was combined with 3 µl of an interphase extract which had been driven into mitosis by the addition of Xenopus cyclin B; and the remaining aliquot was combined with 3 µl of an interphase extract which had similarly been driven into mitosis and which contained mitotic kinases that had been hyperactivated with okadaic acid. After incubation with the respective extracts, the aliquots were boiled in 2% SDS, diluted 20-fold, and immunoprecipitated with MPM-2 immobilized on beads as set forth in Example 5. After five washes with Wash C, the beads were boiled in sample buffer and the Xenopus proteins which bound the MPM-2 antibody were analyzed using 5–15% SDS-polyacrylamide gel electrophoresis as set forth above.

A protein encoded by a single clone was confirmed in its mitosis-specific phosphorylation if it was not precipitated with the MPM-2 monoclonal antibody when it was incubated in an interphase extract, but was precipitated with MPM-2 when incubated with a mitotic extract. Using the methods set forth herein, about 6000 clones of the library of Example 1 have been screened, with the following results. One known protein which is known to be phosphorylated by mitotic kinases was isolated. Seven known proteins which were not previously known to be phosphorylated by mitotic kinases were isolated. Six previously unknown proteins which are phosphorylated by mitotic kinases have been isolated.

Those skilled in the art will recognize, or be able to ascertain, using no more than routine experimentation, numerous equivalents to the specific substances and procedures described herein. Such equivalents are considered to be within the scope of this invention, and are covered by the following claims.

We claim:

1. In a method of identifying a cDNA encoding a desired protein, which method comprises the steps of preparing a cDNA library from a cell that expresses said desired protein; inserting said cDNA library into an expression vector, thereby forming an expression cDNA library; transforming said expression library into bacterial cells and culturing said bacterial cells to produce individual bacterial colonies, wherein each colony contains a member of said expression library; collecting pools of a predetermined number of said individual bacterial colonies; isolating cDNA from said pools of bacterial colonies; expressing proteins encoded by said cDNAs; and identifying a desired protein and the cDNA encoding said desired protein; the improvement comprising:

a) collecting pools of about 100 individual bacterial colonies, wherein each colony contains a member of an expression cDNA library, thereby forming cDNA pools; and b) expressing proteins encoded by the cDNA in said cDNA pools in an in vitro transcription/translation system in a common reaction mixture, and identifying a desired protein from said reaction mixture.

2. The method of claim 1, wherein the desired protein is a nucleic acid binding protein.

3. The method of claim 1, wherein the desired protein is a cytoskeletal protein.

4. The method of claim 1, wherein the desired protein is a growth factor.

5. The method of claim 1, wherein the desired protein is a differentiation factor.

6. The method of claim 1, wherein the desired protein is a post-translationally modified protein.

7. The method of claim 1, wherein the desired protein is a phosphorylated protein.

8. The method of claim 1, wherein the desired protein is a proteolytically cleaved protein.

9. The method of claim 1, wherein the desired protein is a glycosylated protein.

10. The method of claim 1, wherein the desired protein is a subunit of a multiple component protein complex.

11. The method of claim 1, wherein the desired protein is an enzyme.

12. The method of claim 1, wherein the desired protein is an isoform of a known protein.

13. The method of claim 1, wherein the desired protein is a mutant form of a known protein.

14. The method of claim 1, wherein the detecting step comprises radioactive labeling of the expressed proteins.

15. The method of claim 1, wherein the detecting step comprises chemical labeling of the expressed proteins.

* * * * *